United States Patent
Karakelle et al.

(10) Patent No.: US 6,462,082 B2
(45) Date of Patent: Oct. 8, 2002

(54) USE OF HYDROXYEICOSATETRAENOIC ACID DERIVATIVES IN INTRAOCULAR SURGERY

(75) Inventors: Mutlu Karakelle; Kwan Chan, both of Fort Worth, TX (US)

(73) Assignee: Alcon Universal Ltd., Hunenberg (CH)

(*) Notice: Subject to any disclaimer, the term of this patent is extended or adjusted under 35 U.S.C. 154(b) by 0 days.

(21) Appl. No.: 09/965,348

(22) Filed: Sep. 27, 2001

(65) Prior Publication Data

US 2002/0103257 A1 Aug. 1, 2002

Related U.S. Application Data

(60) Provisional application No. 60/242,501, filed on Oct. 23, 2000.

(51) Int. Cl.[7] .................................................. A61K 31/445
(52) U.S. Cl. ........................ 514/530; 514/573; 514/912
(58) Field of Search ................................. 514/530, 573, 514/912

(56) References Cited

U.S. PATENT DOCUMENTS

| | | | |
|---|---|---|---|
| 4,753,945 A | 6/1988 | Gilbard et al. | 514/263 |
| 4,818,537 A | 4/1989 | Guo | 424/427 |
| 4,868,154 A | 9/1989 | Gilbard et al. | 514/13 |
| 4,906,467 A | 3/1990 | Schwartzman et al. | 424/80 |
| 5,455,265 A | 10/1995 | Chandraratna | 514/448 |
| 5,620,921 A | 4/1997 | Sullivan | 514/178 |
| 5,696,166 A | 12/1997 | Yanni et al. | 514/573 |
| 6,353,022 B1 | 3/2002 | Schneider et al. | 514/530 |

OTHER PUBLICATIONS

Barany et al., "The Mucinous Layer Covering the Corneal Endothelium in the Owl Strix Aluco," *Britich J. Ophthalmology*, vol. 41; pp. 25–30 (1957).

Dartt et al., "Vasoactive Intestinal Peptide–Stimulated Glycoconjugate Secretion from Conjunctival Goblet Cells," *Exp. Eye Research*, vol. 63, pp. 27–34 (1996).

Dilly et al., "Surface Changes in the Anesthetic Conjunctiva in Man, with Special Reference to the Production of Mucus from a non–goblet–cell source," *British J. of Ophthalmology*, vol. 65, pp. 833–842 (1981).

Edelhauser, "The Resiliency of the Corneal Endothelium to Refractive and Intraocular Surgery," *Cornea*, vol. 19(3); pp. 263–273 (2000).

Greiner et al., "Mucus Secretory Vesicles in Conjunctival Epithelial Cells of Wearers of Contact Lenses," *Arch. Ophthalmology*, vol. 98, pp. 1843–1846 (1980).

Kim et al., "Corneal Endothelial Damage by Air Bubbles During Phacoemulsification," *Arch. Ophthalmology*, vol. 115, pp. 81–88 (1997).

Marom et al., "Human Airway Monohydroxyeicosatetraenoic Acid Generation and Mucus Release," *J. of Clinical Investigation*, vol. 72, pp. 122–127 (1983).

Nakamura et al., "Gefarnate Stimulates Secretion of Mucin-Like Glycoproteins by Corneal Epithelium in Vitro and protects Corneal Epithelium from Desiccation in Vivo," *Exp. Eye Research*, vol. 65, pp. 569–574 (1997).

Panjwani et al., "Rabbit Corneal Endothelial Cell Surface Glycoproteins," *Investigative Ophthalmology & Vis. Science*, vol. 26, pp. 450–456 (1985).

Sperling et al., "The Surface Coat on Human Corneal Endothelium." *Acta Ophthalmologica*, vol. 58, pp. 96–102 (1980).

Srivastava et al., "Characterization of a 66–Kilodalton Surface Glycoprotein of the Human Corneal Endothelium," *Investigative Ophthalmology & Vis. Science*, vol. 31 (10), pp. 1982–1993 (1990).

Watanabe et al., "Human Corneal and Conjunctival Epithelia Produce a Mucin–like Glycoprotein for the Apical Surface," *Investigative Ophthalmology & Vis. Science*, vol. 36(2) (1995).

Yanni et al., "Effect of Intravenously Administered Lipoxygenase Metabolites on Rat Tracheal Mucous Gel layer Thickness," *International Archives of Allery and Applied Immunology*, vol. 90, pp. 307–309 (1989).

*Primary Examiner*—Zohreh Fay
(74) *Attorney, Agent, or Firm*—Patrick M. Ryan

(57) ABSTRACT

The use of HETE derivatives in intraocular surgery (e.g., cataract surgery) is disclosed. The HETE derivatives protect and maintain the corneal endothelium.

7 Claims, No Drawings

USE OF HYDROXYEICOSATETRAENOIC ACID DERIVATIVES IN INTRAOCULAR SURGERY

This application claims priority to U.S. Provisional Application, U.S. Ser. No. 60/242,501 filed Oct. 23, 2000.

The present invention is directed to the use of hydroxyeicosatetraenoic acid derivatives during intraocular surgery. In particular, the invention relates to the use of such derivatives for the protection of the corneal endothelium during intraocular surgery.

BACKGROUND OF THE INVENTION

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., Mucous Secretory Vesicles in Conjunctival Epithelial Cells of Wearers of Contact Lenses, *Archives of Ophthalmology*, volume 98, pages 1843–1846 (1980); and Dilly et al., Surface Changes in the Anaesthetic Conjunctiva in Man, with Special Reference to the Production of Mucous from a Non-Goblet-Cell Source, *British Journal of Ophthalmology*, volume 65, pages 833–842 (1981)). A number of human-derived mucins which reside in the apical and subapical corneal epithelium have been discovered and cloned (Watanabe et al., Human Corneal and Conjunctival Epithelia Produce a Mucin-Like Glycoprotein for the Apical Surface, *Investigative Ophthalmology and Visual Science*, volume 36, number 2, pages 337–344 (1995)). Recently, Watanabe discovered a new mucin which is secreted via the cornea apical and subapical cells as well as the conjunctival epithelium of the human eye (Watanabe et al., *IOVS*, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, Effect of Intravenously Administered Lipoxygenase Metabolites on Rat Trachael Mucous Gel Layer Thickness, *International Archives of Allergy And Applied Immunology*, volume 90, pages 307–309 (1989)). Similarly, Marom has reported the production of mucosal glycoproteins in human lung by HETE derivatives (Marom et al., Human Airway Monohydroxyeicosatetraenoic Acid Generation and Mucous Release, *Journal of Clinical Investigation*, volume 72, pages 122–127 (1983)).

Agents claimed for increasing ocular mucin and/or tear production include vasoactive intestinal polypeptide (Dartt et. al., Vasoactive intestinal peptide-stimulated glycoconjiugate secretion from conjunctival goblet cells. *Experimental Eye Research*, volume 63, pages 27–34, (1996)), gefarnate (Nakmura et. al., Gefarnate stimulates secretion of mucin-like glycoproteins by corneal epithelium in vitro and protects corneal epithelium from dessication in vivo, *Experimental Eye Research*, volume 65, pages 569–574 (1997)), liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), and retinoids (U.S. Pat. No. 5,455,265). None of these agents, however, have been reported to have an effect on the corneal endothelium.

U.S. Pat. No. 5,696,166 (Yanni et al.) discloses compositions containing HETE derivatives and methods of using them topically for treating dry eye. Yanni et al. discovered that compositions comprising HETE derivatives increase ocular mucin secretion and are thus useful in treating dry eye. This patent does not disclose the use of the HETE derivatives during intraocular surgery for the protection of the corneal endothelium.

During intraocular surgery, such as cataract surgery, the corneal endothelium is susceptible to damage by physical contacts with instrumentation or implants and fluid turbulence and ultrasonic disturbance during phacoemulsification. The corneal endothelium does not regenerate. Corneal endothelial cell damage can lead to a reduction in corneal endothelial cell density and an impairment of ion-pumping function, both of which can lead to corneal edema and visual impairment. Irrigating solutions containing nutrients (ions, glucose, etc.) and/or anti-oxidants have been proposed to maintain or protect the corneal endothelium. Additionally, viscoelastics are used to provide a physical barrier in order to prevent contact damage.

SUMMARY OF THE INVENTION

The present invention is directed to methods of using of HETE derivatives to maintain and protect the corneal endothelium during intraocular surgery. The invention also relates to compositions containing HETE derivatives where the compositions are intended for use during intraocular surgery. Although not wishing to be bound by any theory, it is believed that the HETE derivatives maintain and protect the corneal endothelium by stimulating mucin secretion in the corneal endothelium.

DETAILED DESCRIPTION OF THE INVENTION

As used herein, "HETE derivative" means a compound of formulas I–XI.

I-III:

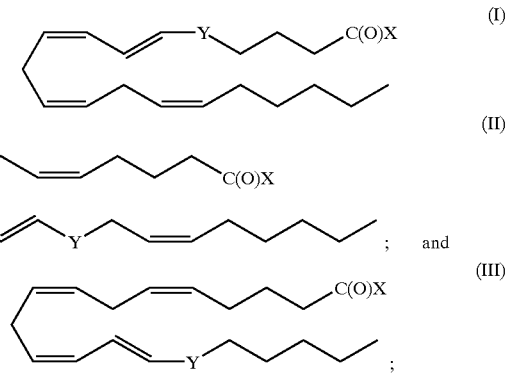

wherein:
X is OR or NHR';
R is H, a cationic pharmaceutically acceptable salt moiety, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;

R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is

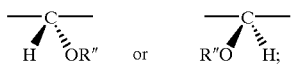

wherein R" is H or C(O)R;

IV:

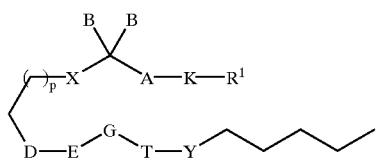

wherein:

R$^1$ is CO$_2$R, CONR$^2$R$^3$, CH$_2$OR$^4$, CH$_2$NR$^5$R$^6$, CH$_2$N$_3$, CH$_2$-Hal, CH$_2$NO$_2$, CH$_2$SR$^{20}$, COSR$^{21}$, or 2,3,4,5-tetrazol-1-yl, wherein:
  R is H or CO$_2$R forms a pharmaceutically acceptable salt or a pharmaceutically acceptable ester;
  NR$^2$R$^3$ and NR$^5$R$^6$ are the same or different and comprise a free or functionally modified amino group, e.g., R$^2$, R$^3$, R$^5$ and R$^6$ are the same or different and are H, alkyl, cycloalkyl, aralkyl, aryl, OH, or alkoxy, with the proviso that at most only one of R$^2$ and R$^3$ are OH or alkoxy and at most only one of R$^5$ and R$^6$ are OH or alkoxy;
  OR$^4$ comprises a free or functionally modified hydroxy group, e.g., R$^4$ is H, acyl; alkyl, cycloalkyl, aralkyl, or aryl;
  Hal is F, Cl, Br or I;
  SR$^{20}$ comprises a free or functionally modified thiol group;
  R$^{21}$ is H, or COSR$^{21}$ forms a pharmaceutically acceptable salt or a pharmaceutically acceptable thioester;
K is C$_2$-C$_8$ alkyl, alkenyl, or alkynyl, or a C$_3$-C$_8$ allenyl group;
A and X are the same or different and are a direct bond, CH$_2$, NR$^7$, O, or S, with the proviso that at least one of A and X is NR$^7$, O, or S;
B is H, or BB together comprises a double bonded O, S, or NR$^8$, with the proviso that BB comprises a double bonded O, S, or NR$^8$ when A and X are the same or different and are NR$^7$, O, or S; wherein:
  NR$^7$ and NR$^8$ are the same or different and comprise a functionally modified amino group, e.g., R$^7$ and R$^8$ are the same or different and are H, alkyl, cycloalkyl, aryl, aralkyl, acyl, OH, or alkoxy;
is 0 or 1;
D—E, G—H are the same or different and are CH$_2$CH$_2$, CH=CH, or C≡C; and Y is C(O) (i.e. a carbonyl group) or Y is

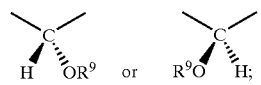

wherein R$^9$O constitutes a free or functionally modified hydroxy group;

V:

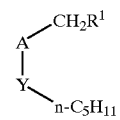

wherein:
  R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$, or 2,3,4,5-tetrazol-1-yl, where:
    R is H or a pharmaceutically acceptable cation, or CO$_2$R forms a pharmaceutically acceptable ester moiety;
    NR$^2$R$^3$, NR$^5$R$^6$ are the same or different and comprise a free or functionally modified amino group;
    OR$^4$ comprises a free or functionally modified hydroxy group;
    Hal is F, Cl, Br, or I;
    R$^{20}$ is H, alkyl, acyl;
    R$^{21}$ is H or a pharmaceutically acceptable cation, or COSR$^{21}$ forms a pharmaceutically acceptable thioester moiety;
A is L$_1$—A$_1$—L$_2$, L$_1$—A$_2$—L$_2$, L$_3$—A$_2$—L$_4$, or L$_5$—A$_2$—L$_3$;
A$_1$ is CH$_2$CH$_2$;
A$_2$ is

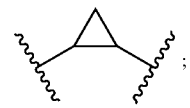

L$_1$ is CH$_2$—B—D;
  B and D are the same or different and are CH$_2$CH$_2$, CH=CH, or C≡C;
L$_2$ is CH$_2$—K—CH$_2$CH$_2$;
  K is CH$_2$CH$_2$, CH=CH, or C≡C;
L$_3$ is CH$_2$CH$_2$CH$_2$, CH$_2$CH=CH, CH$_2$C≡C, CH=CHCH$_2$, C≡CCH$_2$, or CH=C=CH;
L$_4$ is X—CH$_2$CH$_2$;
  X is CH$_2$CH$_2$CH=CH, CH$_2$CH$_2$C≡C, CH$_2$CH$_2$CH$_2$CH$_2$, CH$_2$CH=CHCH$_2$, CH$_2$C≡CCH$_2$, CH=CHCH$_2$CH$_2$, C≡CCH$_2$CH$_2$, CH$_2$CH=C=CH, or CH=C=CHCH$_2$;
L$_5$ is CH$_2$CH$_2$—B—D; and
Y is C(O) (i.e. a carbonyl group) or Y is

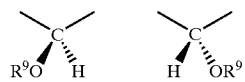

wherein R$^9$O constitutes a free or functionally modified hydroxy group;

VI:

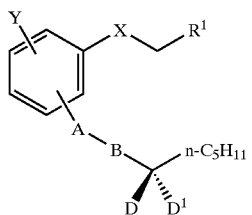

wherein:
- $R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
    - R is H or $CO_2R$ forms a pharmaceutically acceptable salt or a pharmaceutically acceptable ester;
    - $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH or alkoxy, with the proviso that at most only one of $R^2$ and $R^3$ are OH or alkoxy and at most only one of $R^5$ and $R^6$ are OH or alkoxy;
    - $OR^4$ comprises a free or functionally modified hydroxy group, e.g., $R^4$ is H, acyl; alkyl, cycloalkyl, aralkyl or aryl;
    - Hal is F, Cl, Br or I;
    - $SR^{20}$ comprises a free or functionally modified thiol group;
    - $R^{21}$ is H or $COSR^{21}$ forms a pharmaceutically acceptable salt or a pharmaceutically acceptable thioester;
- X is $C_2$–$C_5$ alkyl, alkynyl, or alkenyl or a $C_3$–$C_5$ allenyl group;
- Y is H, free or functionally modified hydroxy group, halo, trihalomethyl, free or functionally modified amino group, free or functionally modified thiol group, C(O)$R^7$, or alkyl;
- $R^7$ is H, OH, alkyl, alkoxy, amino, alkylamino or alkoxyamino;
- A is a direct bond or $C_{1-3}$ alkyl;
- B is $CH_2CH_2$, cis- or trans-CH=CH, or C≡C; and
- one of D and $D^1$ is H and the other is a free or functionally modified OH group, or $DD^1$ together comprises a double bonded oxygen;

VII:

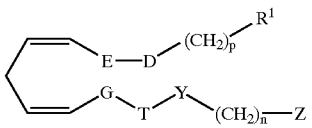

wherein:
- $R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
    - R is H or $CO_2R$ forms a pharmaceutically acceptable salt or a pharmaceutically acceptable ester;
    - $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
    - $OR^4$ comprises a free or functionally modified hydroxy group, e.g., $R^4$ is H, acyl; alkyl, cycloalkyl, aralkyl or aryl;
    - Hal is F, Cl, Br or I;
    - $SR^{20}$ comprises a free or functionally modified thiol group;
    - $R^{21}$ is H or $COSR^{21}$ forms a pharmaceutically acceptable salt or a pharmaceutically acceptable thioester;
- E—D is $CH_2CH_2CH_2$ or cis-$CH_2CH$=CH; or E is trans-CH=CH and D is CH(OH) in either configuration, wherein the OH is free or functionally modified; or E is $CH_2CH_2$ and D is a direct bond;
- p is 1 or 3 when E—D is $CH_2CH_2CH_2$ or cis-$CH_2CH$=CH, or when E is trans-CH=CH and D is CH(OH) in either configuration, wherein the OH is free or functionally modified; or p is 0 when E is $CH_2CH_2$ and D is a direct bond;
- G—T is $CH_2CH_2$, $CH(SR^7)CH_2$ or trans-CH=CH;
- $R^7$ is H, alkyl, aryl, aralkyl, cycloalkyl or acyl;
- Y is CH(OH) in either configuration, in which the OH is free of functionally modified, or C=O (i.e., a carbonyl group);
- n is 0, 2 or 4; and
- Z is $CH_3$, $CO_2R$, $CONR^2R^3$ or $CH_2OR^4$;

VIII:

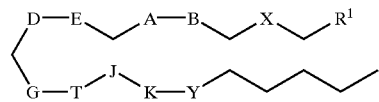

wherein:
- $R^1$ is $(CH_2)_nCO_2R$, $(CH_2)_nCONR^2R^3$, $(CH_2)_nCH_2OR^4$, $(CH_2)_nCH_2NR^{5R6}$, $(CH_2)_nCH_2N_3$, $(CH_2)_nCH_2Hal$, $(CH_2)_nCH_2NO_2$, $(CH_2)_nCH_2SR^{20}$, $(CH_2)_nCOSR^{21}$ or $(CH_2)_n$-2,3,4,5-tetrazol-1-yl, wherein:
    - R is H or $CO_2R$ forms a pharmaceutically acceptable salt or a pharmaceutically acceptable ester;
    - $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl aralkyl, aryl, OH, or alkoxy, with the proviso that at most only one of $R^2$ and $R^3$ are OH or alkoxy and at most only one of $R^5$ and $R^6$ are OH or alkoxy;
    - $OR^4$ comprises a free or functionally modified hydroxy group, e.g., $R^4$ is H, acyl; alkyl, cycloalkyl, aralkyl, or aryl;
    - Hal is F, Cl, Br or I;
    - $SR^{20}$ comprises a free or functionally modified thiol group;
    - $R^{21}$ is H or $COSR^{21}$ forms a pharmaceutically acceptable salt or a pharmaceutically acceptable thioester;
- n is 0 or 2;
- X is O, S(O)$_p$, $NR^7$ or $CH_2$, with the proviso that X cannot be $CH_2$ when n is 0;
- p is 0, 1 or 2;
- $NR^7$ comprises a free or functionally modified amino group, e.g., $R^7$ is H, alkyl, cycloalkyl, aralkyl, aryl, OH or alkoxy,
- A—B, D—E, G—T and J—K are the same or different and are $CH_2CH_2$, CH=CH or C≡C, with the proviso that at least one of A—B, D—E, G—T and J—K must be CH=CH or C≡C; and Y is C(O) (i.e., a carbonyl), or Y is

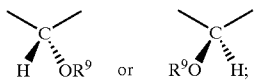

wherein $R^9O$ constitutes a free or functionally modified hydroxy group;

IX:

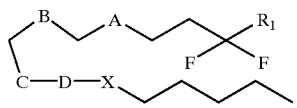

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
$OR^4$ comprises a free or functionally modified hydroxy group, e.g., $R^4$ is H, acyl; alkyl, cycloalkyl, aralkyl, or aryl;
Hal is F, Cl, Br or I;
$SR^{20}$ comprises a free or functionally modified thiol group;
$R^{21}$ is H or $COSR^{21}$ forms a pharmaceutically acceptable salt or a pharmaceutically acceptable thioester;
A, B, C and D are the same or different and are $C_1$–$C_5$ alkyl, alkenyl, or alkynyl or a $C_3$–$C_5$ allenyl group;
X is C(O) (i.e. a carbonyl group) or X is

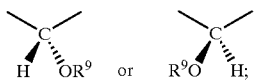

wherein $R^9O$ constitutes a free or functionally modified hydroxy group;

X:

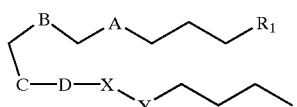

wherein:
$R^1$ is $(CH_2)_nCO_2R$, $(CH_2)_nCONR^2R^3$, $(CH_2)_nCH_2OR^4$, $(CH_2)_nCH_2NR^5R^6$, $(CH_2)_nCH_2N_3$, $(CH_2)_nCH_2Hal$, $(CH_2)_nCH_2NO_2$, $(CH_2)_nCH_2SR^{20}$, $(CH_2)_nCOSR^{21}$ or $(CH_2)_n$-2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
$OR^4$ comprises a free or functionally modified hydroxy group, e.g., $R^4$ is H, acyl; alkyl, cycloalkyl, aralkyl, or aryl;
Hal is F, Cl, Br or I;
$SR^{20}$ comprises a free or functionally modified thiol group;
$R^{21}$ is H or $COSR^{21}$ forms a pharmaceutically acceptable salt or a pharmaceutically acceptable thioester;
n is 0 or 2;
A, B, C and D is $C_1$–$C_5$ alkyl, alkenyl, or alkynyl or a $C_3$–$C_5$ allenyl group;
Y is

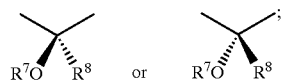

wherein $R^8$ is H or $CH_3$, and
X is $CH_2$, $CH(CH_3)$ or $C(CH_3)_2$; or
Y is $CH_2$, $CH(CH_3)$ or $C(CH_3)_2$, and X is

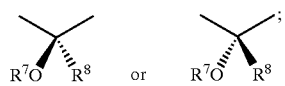

wherein $R^8$ is H or $CH_3$, with the proviso that Y cannot be $CH_2$ when X is

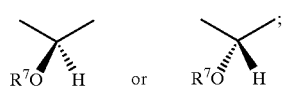

and
$R^7O$ comprises a free or functionally modified hydroxy group; and

XI:

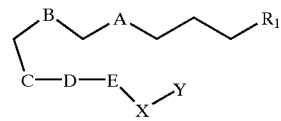

wherein:
R is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:
R is H or a pharmaceutically acceptable cation, or $CO_2R$ forms a pharmaceutically acceptable ester moiety;
$NR^2R^3$, $NR^5R^6$ are the same or different and comprise a free or functionally modified amino group;
$OR^4$ comprises a free or functionally modified hydroxy group;
Hal is F, Cl, Br, or I;
$SR^{20}$ comprises a free or functionally modified thiol group;

R²¹ is H or a pharmaceutically acceptable cation, or COSR²¹ forms a pharmaceutically acceptable thioester moiety;

A, B, C, D are the same or different and are $C_1$–$C_5$ alkyl, $C_2$–$C_5$ alkenyl, $C_{1-5}$ cyclopropyl, $C_2$–$C_5$ alkynyl, or a $C_3$–$C_5$ allenyl group;

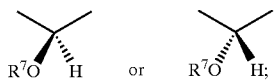

where OR⁷ comprises a free or functionally modified hydroxy group;

X=$(CH_2)_m$ or $(CH_2)_mO$, where m=1–6; and

Y=a phenyl ring optionally substituted with alkyl, halo, trihalomethyl, acyl, or a free or functionally modified hydroxy, amino, or thiol group; or X—Y=$(CH_2)_pY^1$; where p=0–6; and

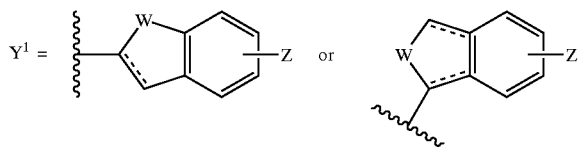

wherein:

W=$CH_2$, O, $S(O)_q$, NR⁸, $CH_2CH_2$, CH=CH, $CH_2O$, $CH_2S(O)_q$, CH=N, or $CH_2NR^8$; where q=0–2, and R⁸=H, alkyl, or acyl;

Z=H, alkyl, acyl, halo, trihalomethyl, or a free or functionally modified amino, thiol, or hydroxy group; and ----=single or double bond;

or X—Y=cyclohexyl.

Preferred HETE derivatives include the compounds of formulas I–III wherein X is a pharmaceutically acceptable salt containing a cation selected from the group consisting of: Na⁺; K⁺; Li⁺; Cs⁺; and (A)₄N⁺; and A is independently H, alkyl, cycloalkyl, (cycloalkyl)alkyl, alkyl(cycloalkyl), aryl, arylalkyl, heteroaryl, or (A)₄N⁺forms a heteroaryl, heterocycloalkenyl or heterocycloalkyl ring.

Included within the scope of the present invention are the individual enantiomers of the HETE derivatives, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "$C_1$–$C_5$ cyclopropyl" means an alkyl chain of 1 to 5 carbon atoms containing a cyclopropyl group wherein the cyclopropyl group may start, be contained in or terminate the alkyl chain.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon-carbon double bond, the chain being optionally interrupted by one or more heteroatoms. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

According to the methods of the present invention a HETE derivative of formulas I–XI is applied intraocularly in connection with intraocular surgery. The compositions used in the methods of the present invention comprise a pharmaceutically effective amount of one or more HETE derivatives of formulas I–XI and a pharmaceutically acceptable carrier. Suitable pharmaceutical carriers are those that can be used in connection with intraocular surgery and include, but are not limited to, ophthalmically acceptable surgical irrigating solutions and ophthalmically acceptable viscoelastic materials. Many such irrigating solutions and viscoelastic materials are known. Examples of irrigating solutions include, but not limited to, BSS® and BSS PLUS® irrigating solutions (Alcon Laboratories, Inc.). Examples of viscoelastics include, but are not limited to, CELLUGEL®, VISCOAT® and PROVISC® viscoelastics (Alcon Laboratories, Inc.) and HEALON® and HEALON® GV viscoelastics (Pharmacia Corporation).

As used herein, the term "pharmaceutically effective amount" refers to an amount of one or more compounds of formula (I) that, when administered to a patient, protects or helps maintain the corneal endothelium. Generally, the compounds of formula (I) will be contained in a composition of the present invention in a concentration range of about 0.00001 to 10 per cent weight/volume ("% w/v"). Preferably, the compositions will contain one or more compounds of formula (I) in a concentration of from about 0.00001–0.01 % w/v.

In one embodiment, the compositions of the present invention will also contain ethanol. As used herein, "an effective concentration of ethanol" refers to a concentration that enhances the biological efficacy of the formula (I) compositions in vivo. In general, the concentration of ethanol necessary for the enhancement of the compounds of formula (I) is believed to be somewhat proportional to the concentration of the formula (I) compound(s) administered. If a relatively high concentration of formula (I) compound (s), e.g., above 0.1% w/v, is administered, the concentration of ethanol in such compositions may be proportionally less than analogous compositions containing lower concentrations of formula (I) compounds. In general, however, the ethanol concentration contained in the ophthalmic compositions of the present invention will range from about 0.001–2% w/v. Compositions containing formula (I) concentrations of about 0.00001–0.05% w/v preferably will contain ethanol in a concentration of about 0.005–0.40% w/v, and most preferably, about 0.02–0.20% w/v.

Various tonicity agents may be included in the compositions of the present invention to adjust tonicity, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have one or more tonicity agents in a total concentration sufficient to cause the composition to have an osmolality of about 200–400 mOsm.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. In general, however, the buffering agent will be present in an amount sufficient to hold the pH within the range 6.5–8.0, preferably 6.8–7.6.

Antioxidants may be added to compositions of the present invention to protect the formula (I) compounds from oxidation during storage and/or or to provide antioxidant effects in the eye. Examples of such antioxidants include, but are not limited to, vitamin E and analogs thereof, ascorbic acid and derivatives, and butylated hydroxyanisole (BHA).

The following examples are presented to illustrate various aspects of the present invention, but are not intended to limit the scope of the invention in any respect.

EXAMPLE 1

Two-Part Irrigating Solution (Use Within 6 Hours of Reconstitution):

| Ingredient | Concentration (% w/v) |
|---|---|
| Part I (approx. 480 mL) | |
| HETE derivative | 0.00001–0.01 |
| NaCl | 0.7–0.8 |
| KCl | 0.03–0.04 |
| Dibasic Sodium Phosphate | 0.04–0.05 |
| Sodium Bicarbonate | 0.2–0.3 |
| HCl/NaOH | pH adjust to 7.4 |
| Water for injection | qs 100 |
| Part II (approx. 20 mL) | |
| Glutathione Disulfide | 0.4–0.5 |
| Calcium Chloride (Dihydrate) | 0.3–0.4 |
| Magnesium Chloride (Hexahydrate) | 0.4–0.6 |
| Dextrose (Anhydrous) | 2–3 |
| Water for injection | qs 100 |

EXAMPLE 2

Viscoelastic Composition:

| Ingredient | Concentration (% w/v) |
|---|---|
| HETE derivative | 0.00001–0.01 |
| Sodium Chondroitin Sulfate | 3.5–4 |
| Hyaluronic Acid (Sodium Salt) | 2.9–3 |
| NaCl | 0.3–0.5 |
| Dibasic Sodium Phosphate (Anhydrous) | 0.15–0.25 |
| Monobasic Sodium Phosphate (Monohydrate) | 0.04–0.05 |
| HCl/NaOH | pH adjust to 7.4 |
| Water for injection | qs 100 |

The invention in its broader aspects is not limited to the specific details shown and described above. Departures may be made from such details within the scope of the accompanying claims without departing from the principles of the invention and without sacrificing its advantages.

What is claimed is:

1. A method of maintaining and protecting the corneal endothelium during intraocular surgery comprising the intraocular application of a composition comprising one or more HETE derivatives.

2. The method of claim 1 wherein the HETE derivative is a compound of the formula

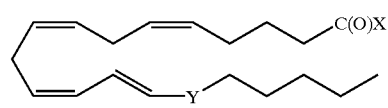

wherein

X is OR or NHR';

R is H, a cationic pharmaceutically acceptable salt moiety, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;

R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is

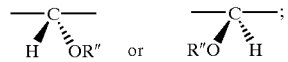

wherein R" is H or C(O)R.

3. The method of claim 2 wherein R is selected from the group consisting of: $Na^+$; $K^+$; $Li^+$; $Cs^+$; and $(A)_4N^+$; and A is independently H, alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring.

4. The method of claim 1 wherein the composition is selected from surgical irrigating solutions and viscoelastic compositions.

5. The method of claim 1 wherein the HETE derivative is present in the composition in a concentration range of about 0.00001 to 10% w/v.

6. The method of claim 5 wherein the concentration range is about 0.00001–0.01% w/v.

7. The method of claim 1 wherein the composition comprises ethanol.

* * * * *